United States Patent [19]

Onopchenko et al.

[11] 4,157,353

[45] Jun. 5, 1979

[54] PROCESS FOR RECOVERING A DIALKYLARYLKETONE

[75] Inventors: Anatoli Onopchenko, Monroeville; Johann G. Schulz, Pittsburgh, both of Pa.

[73] Assignee: Gulf Research & Development Company, Pittsburgh, Pa.

[21] Appl. No.: 871,239

[22] Filed: Jan. 23, 1978

Related U.S. Application Data

[63] Continuation-in-part of Ser. No. 782,630, Mar. 30, 1977, Pat. No. 4,093,660.

[51] Int. Cl.$^2$ ............................................. C07C 49/76
[52] U.S. Cl. .................................................. 260/591
[58] Field of Search ........................................ 260/591

[56] References Cited

U.S. PATENT DOCUMENTS

| | | | |
|---|---|---|---|
| 3,403,183 | 9/1968 | Dobratz et al. | 260/591 |
| 4,018,828 | 4/1977 | Onopchenko et al. | 260/591 |
| 4,093,660 | 6/1978 | Onopchenko et al. | 260/591 |

*Primary Examiner*—James H. Reamer

[57] ABSTRACT

A process for recovering a dialkylarylketone from an oily mixture containing largely a 1,1-diaryl-2-nitroethylene as contaminant which comprises heating the oily mixture to a temperature of at least about 140° C. and then recovering solid dialkylarylketone from a solvent solution of the 1,1-diaryl-2-nitroethylene.

23 Claims, No Drawings

PROCESS FOR RECOVERING A DIALKYLARYLKETONE

This application is a continuation-in-part application of our application Ser. No. 782,630, filed Mar. 30, 1977 now U.S. Pat. No. 4,093,660, for PROCESS FOR RECOVERING A DIALKYLARYLKETONE, which application is incorporated herein by reference.

BACKGROUND OF THE INVENTION

1. Field of the Invention

The invention defined herein relates to a process for recovering a di(alkylaryl)ketone, normally solid at room temperature (26° C.), from an oily liquid mixture containing the same.

2. Description of the Prior Art

In our U.S. Pat. No. 4,018,828, dated Apr. 19, 1977 entitled Process for Recovering a Dialkylarylketone, we found we were able to recover a dialkylarylketone, particularly tetramethylbenzophenone, from an oily mixture containing largely the corresponding 1,1-diaryl-2-nitroethylene as a contaminant by adding a base, such as sodium hydroxide, to the mixture until solidification occurred and then effecting the desired recovery of benzophenone from a suitable solvent.

SUMMARY OF THE INVENTION

The process defined and claimed herein relates to the recovery of a dialkylarylketone, specifically, 3,4,3',4'-tetramethylbenzophenone (TMB) or 4,4'-dimethylbenzophenone (DMB), from an oily mixture contaminated largely with a 1,1-diaryl-2-nitroethylene, specifically, 1,1-di(3,4-dimethylphenyl)-2-nitroethylene when TMB is the dialkylarylketone, or 1,1-di(4-methylphenyl)-2-nitroethylene when DMB is the dialkylarylketone, which comprises heating the mixture to a temperature of at least about 140° C. and then recovering the dialkylarylketone from a solvent solution of the 1,1-diaryl-2-nitroethylene.

BRIEF DESCRIPTION OF THE PROCESS

The oily mixture being treated herein will contain the following components in the following amounts:

| | Parts by Weight | |
|---|---|---|
| | Broad Range | Narrow Range |
| 3,4,3',4'-tetramethylbenzophenone (TMB) or 4,4'-dimethylbenzophenone (DMB) | 25 to 95 | 55 to 90 |
| 1,1-di(3,4-dimethylphenyl)-2-nitroethylene (DMPE) or 1,1-di(4-methylphenyl)-2-nitroethylene (MPE) | 5 to 40 | 10 to 30 |
| 1,1-di(3,4-dimethylphenyl)ethanol (DMPET) or 1,1-di(4-methylphenyl)ethanol (MPET) | 0 to 5 | 0 to 2 |
| Compounds corresponding to the above wherein one or more methyl substituents are converted to carboxyl | 0 to 15 | 0 to 5 |
| 1,1-bis(3,4-dimethylphenyl)ethane (DXE) or 1,1-bis(p-tolyl)ethane (DTE) | 0 to 50 | 0 to 25 |

In a preferred embodiment, the oily mixture treated herein is obtained as a result of the nitric acid oxidation of DXE or DTE at a temperature below about 140° C., but above about 70° C., using critical amounts of nitric acid and water as defined and claimed, for example, in our U.S. Pat. No. 4,022,838, dated May 10, 1977, entitled Process for Preparing Diarylketones.

In accordance with our discovery, we heat the oily mixture defined above to a temperature of at least about 140° C., preferably at least about 160° C., but no higher than about 300° C., preferably no higher than about 225° C., for at least about one minute, preferably at least about 15 minutes, but generally no longer than about two hours, preferably no longer than about 60 minutes. Pressures are not critical and therefore any suitable pressure can be used. Thus the pressure can be from about 14.7 pounds per square inch gauge, or atmospheric, (about one kilogram per square centimeter) to about 1000 pounds per square inch gauge (about 68 kilograms per square centimeter), preferably about 14.7 pounds per square inch gauge to about 300 pounds per square inch gauge (about 20 kilograms per square centimeter).

As a result of such heating, the oily mixture will unexpectedly solidify to form particulate solids, generally yellow to pale green in color. The TMB or DMB present is recovered from said solids by recrystallization from a solvent. Any solvent in which TMB or DMB is substantially insoluble at room temperature but the remaining compounds associated therewith are substantially soluble can be used. Examples of solvents suitable herein include alcohols, such as methanol, ethanol and isopropanol; esters, such as methyl acetate, ethyl acetate and methyl formate; ketones, such as acetone, methylethylketone and cyclohexanone; organic acids, such as acetic acid and propionic acid; ethers, such as tetrahydrofuran and dioxane; hydrocarbons, such as benzene, toluene, n-hexane and n-heptane; chlorinated hydrocarbons, such as carbon tetrachloride, methylene chloride, chloroform and chlorobenzenes; "super-solvents", such as dimethylsulfoxides, dimethylformamide and hexamethylphosphoramide; carbon disulfide; etc. The amount of solvent used can vary over a wide limit, but in general the weight ratio of solid to solvent will be in the range of about 1:100 to about 1:1, preferably in the practical range of about 5:100 to about 1:4.

The recrystallization of TMB or DMB is easily effected. The solids, defined above, are stirred with the solvents, defined above, at a temperature of from about 26° C. to about 200° C., preferably from about 26° C. to about 100° C., and a pressure in the ranges defined in the heating step above for a time sufficient to obtain a homogeneous solution, for example, from about five minutes to about one hour, preferably about 10 to about 30 minutes. At the end of this period, the homogeneous mixture is allowed to cool to a temperature of about 0° to about 100° C., preferably about 25° to about 45° C., over a period of about 15 minutes to about two hours, preferably about 30 to about 60 minutes, as a result of which the TMB or DMB will recrystallize out of solution. Simple mechanical separation, for example, filtration, will result in the recovery of TMB or DMB. The filtrate will contain the compounds associated with the TMB or DMB. If the former may still contain some impurities after the above separation, further recrystallization of the TMB or DMB from the solvents, as defined above, will result in a further purification thereof.

An alternative separation procedure to the one defined above involves adding the solvent to the oily mixture prior to the initial heating, but otherwise identical thereto.

DESCRIPTION OF PREFERRED EMBODIMENTS

EXAMPLE I

Into a one-liter, three-necked, round-bottomed flask equipped with a condenser, thermometer and stirrer there was added 140 grams of DXE, 330 grams of water and 75 grams of 70 percent aqueous nitric acid. The mixture was heated under reflux (100° C.,) and atmospheric pressure (14.7 pounds per square inch gauge, or one kilogram per square centimeter) for four hours. After the reaction mixture was cooled to about 0° C., the resulting aqueous layer was separated from the organic layer by decantation. The organic layer of 178 grams lost about 3.1 grams of water upon evaporation to dryness in a rotary evaporator. Analysis of the organic oily liquid (175 grams) by gas chromatography showed the following composition: 15.2 parts by weight, or weight percent, of DXE, 73.9 parts by weight, or weight percent, of TMB, 9.6 parts by weight, or weight percent, of nitroolefin, and 1.3 parts by weight, or weight percent, of unidentified products. Attempts to isolate TMB from the oily mixture by the following series of experiments were unsuccessful.

From about 2.0 to about 2.5 grams of the oily product obtained above were added to each of the following solvents at room temperature and atmospheric pressure (14.7 pounds per square inch gauge) while stirring: methanol, acetone, n-hexane, benzene, ethyl acetate, carbon tetrachloride, acetic acid, p-dioxane, tetrahydrofuran, chloroform and isopropanol. In each instance the product dissolved readily. Each solution was seeded by adding approximately 0.1 gram of pure TMB in an attempt to prompt crystallization of the TMB in the product. No crystallization occurred, even at the end of one day. An attempt was similarly made to seed about 2.5 grams of the oily product, in the absence of a solvent, with pure TMB, but this effort was similarly unsuccessful.

Each of the above solutions was heated at the reflux temperature of the respective solvents for about 15 to 20 minutes and then permitted to come to room temperature and stand for one to two hours. No solids were formed.

Each of the above solutions was then cooled in a dry ice-acetone mixture to about −70° C. and maintained at said temperature for about 10 to 20 minutes until solids formed. The cooled product was permitted to come to room temperature, at which point everything was in solution.

Finally, each of the above solutions was concentrated by evaporation on a steam bath until about ⅔ of the solvent was evaporated therefrom. The solution was permitted to come to room temperature, but no solid formation occurred.

EXAMPLE II

A 700-ml, 314 stainless steel autoclave (Autoclave Engineers Inc., Erie, Pa.) was charged with 140 grams of DXE and 70 grams of water and then heated to a temperature of about 100° C., developing a pressure of 17 pounds per square inch gauge (1.2 kilograms per square centimeter). At this temperature a mixture of 100 grams of 70 percent aqueous nitric acid and 150 grams of water was added to the reactor over a period of 105 minutes. Reaction was continued for an additional hour at 100° C. to a final pressure of about 186 pounds per square inch gauge (13 kilograms per square centimeter). The reactor was cooled to room temperature, depressured to atmospheric pressure and the aqueous solution withdrawn therefrom by suction. The organic oily layer was transferred to a flask, using small amounts of acetone to recover residual material stuck to the walls of the autoclave, and then subjected to evaporation in a rotary evaporator to remove acetone therefrom. A total of 172.4 grams of an oily, viscous fluid was recovered having the following composition: 61.8 parts by weight, or weight percent, of TMB, 14.7 parts by weight, or weight percent, of nitroolefin, 6.6 parts by weight, or weight percent, of unidentified products and 16.9 parts by weight, or weight percent, of DXE. DXE conversion amounted to 80.0 percent. The oily product was found to be completely soluble in common organic solvents, including benzene, acetone and methanol, at room temperature and atmospheric pressure. When 95 grams of the oily product was subjected to distillation under a vacuum of 3 millimeters of mercury in order to effect a separation of its components, unexpectedly before any distillation took place, at a pot temperature of about 150° C., the entire material in the distillation flask solidified to a yellow solid. The remainder of the oily product was transferred back to the reactor and simply heated to a temperature of 175° C. at autogeneous pressure for 15 minutes and then cooled to room temperature (25° C.). Again, the product was a yellow solid. 70 grams of these solids were stirred with 200 cubic centimeters of n-hexane at room temperature and room pressure for five minutes and the resultant mixture was filtered to recover free-flowing solids of the following composition: 73.1 parts by weight, or weight percent, of TMB, 19.6 parts by weight, or weight percent, of nitroolefin, two parts by weight, or weight percent, of DXE and 4.4 parts by weight, or weight percent, of unidentified products. 20 grams of the recovered product were dissolved by stirring in 100 cubic centimeters of methanol at 35° C. and atmospheric pressure. On standing at room temperature for 30 minutes solid product started to precipitate out of solution. Upon filtration, 17.1 grams of a solid product containing 98 weight percent TMB was recovered.

EXAMPLE III

A mixture containing 30 grams of DXE, 330 grams of water and 75 grams of 70 aqueous nitric acid was heated while stirring at atmospheric pressure and a temperature of 100° C. for 3.5 hours. At the end of the reaction, the mixture was cooled to room temperature and the aqueous phase was separated from the oily liquid organic phase by decantation. Analysis by gas chromatography showed the product to have the following composition: 10.6 parts by weight, or weight percent, of DXE, 62.0 parts by weight, or weight percent, of TMB, 25.8 parts by weight, or weight percent, of nitroolefin and 1.6 parts by weight, or weight percent, of unidentified products. The product was diluted with methanol to a final volume of about 240 milliliters and heated to 165° C. and atmospheric pressure for about 30 minutes. The resulting product was cooled to room temperature and filtered to recover 12.7 grams of light tan, free-flowing, solid containing 95.4 weight percent TMB. Further recrystallization of this product from 20 cubic centimeters of methanol which had been heated to a temperature of 40° C. for 10 minutes and cooled to room temperature and maintained at the latter temperature for about 30 minutes, increased the purity of ketone to 98 percent.

EXAMPLE IV

The nitric acid oxidation reaction described in Example II was repeated to obtain an oily mixture analyzing as follows: 62.4 weight percent TMB, 16.6 weight percent nitroolefin, 14.8 weight percent DXE and 6.2 weight percent unidentified products. This mixture was divided into two equal portions, the first was diluted with 200 cubic centimeters of ethyl acetate and the second with 200 cubic centimeters of tetrahydrofuran. Each of the solutions was heated, while stirring, to about 165° C. and autogeneous pressure for about 15 to 20 minutes and then cooled to room temperature and maintained at the latter temperature for 60 minutes. Each of the resulting mixtures was filtered to recover a free-flowing solid. The solids obtained from treatment with ethyl acetate were found to contain 95.1 weight percent TMB, those obtained as a result of treatment with tetrahydrofuran were found to contain 96.2 weight percent TMB.

EXAMPLE V

Into a one-liter, 316-stainless steel, magnetically stirred autoclave (Autoclave Engineers, Inc., Erie, Pa.) equipped with a heater and cooling coils there was charged 105 grams of DXE and 100 grams of water. The autoclave was heated to 110° C., developing a pressure of about 30 pounds per square inch gauge (about 2.1 kilograms per square centimeter), at which point 97 grams of 54 percent aqueous nitric acid were added using a Milroy pump over a period of ten minutes. Reaction was continued for 60 minutes, developing a final pressure of 160 pounds per square inch gauge (11.3 kilograms per square centimeter). The autoclave was cooled to 25° C., and 120 milliliters of aqueous layer was withdrawn by siphoning. The organic layer was transferred to a round-bottomed flask, using about 100 milliliters of methanol to recover residual product adhering to the sides of the reactor, and the mixture was then evaporated to dryness in a rotary evaporator to give 117 grams of a viscous organic product. Analysis by gas-liquid chromatography showed 73 parts by weight of TMB, 17.2 parts by weight of nitroolefin, 1.3 parts by weight of DXE, 1.2 parts by weight of dinitroolefin and 7.3 parts by weight of unidentified reaction intermediates. DXE conversion in this experiment was 98.5 percent, while the nitric acid consumption was 93 percent.

EXAMPLE VI

In this experiment 50 gram samples of the reaction product obtained in Example V were heated in an autoclave to 160° C. and autogeneous pressure for 15 minutes in the presence of 200 milliliters of acetone and 200 milliliters of acetic acid and then cooled to 25° C. The product was filtered through a medium porosity glass-cindered funnel and dried. The results obtained are summarized below:

| Reaction Product (Grams) | Solvent (Milliliters) | TMB Recovered, Grams (Per Cent) | Purity Gas Liquid Chromotography |
|---|---|---|---|
| 50 | Acetone (100) | 16.3 (45) | 99+% |
| 50 | Acetic Acid (200) | 23.7 (65) | 98% |

After recovery of the first crop of product from the acetone solution, the filtrate was concentrated to about 100 milliliters and cooled to 25° C. After standing at this temperature for two hours, an additional 14.3 grams of product (second crop) was recovered. The purity of this material was found to be 93 percent by gas liquid chromatography, corresponding to recovery of about 85 percent of available TMB in the product. No attempt was made to recover additional TMB from the filtrate containing acetic acid.

EXAMPLE VII

Example V was repeated but using 175 milliliters of water instead of 100 milliliters of water. On work-up as before, 129 grams of a viscous organic product was obtained. Analysis by gas liquid chromatography showed the following composition: 69.3 parts by weight of TMB, 19.4 parts by weight of nitroolefin, 1.8 parts by weight of dinitroolefin, 1.2 parts by weight of DXE and 8.3 parts by weight of various intermediates.

EXAMPLE VIII 50 grams of the reaction product obtained in Example VII was heated to 165°-170° C. for 15 minutes in 150 milliliters of chlorobenzene and then cooled to 25° C. After standing for two hours at this temperature, the solids that formed were filtered to recover 20.7 grams (97 percent purity) of TMB, corresponding to a TMB recovery of 57.7 percent. Concentration of the filtrate led to recovery of an additional 7.9 grams of a second crop product (95 percent purity) material, corresponding to about 81 percent TMB recovery.

Obviously, many modifications and variations of the invention, as hereinabove set forth, can be made without departing from the spirit and scope thereof, and therefore only such limitations should be imposed as are indicated in the appended claims.

We claim:

1. A process for recovering a dialkylarylketone selected from the group consisting of 3,4,3',4'-tetramethylbenzophenone and 4,4'-dimethylbenzophenone from an oily mixture contaminated largely with the corresponding 1,1-diaryl-2-nitroethylene, said oily mixture having been obtained as a result of the nitric acid oxidation of a diarylalkane selected from the group consisting of 1,1-bis(p-tolyl)ethane and 1,1-bis(3,4-dimethylphenyl) ethane at a temperature below about 140° C. which comprises heating said mixture to a temperature of at least about 140° until solidification occurs and then recovering the dialkylarylketone as a solid from a solvent solution of the 1,1-diaryl-2-nitroethylene, said solvent being selected from the group consisting of ketones, organic acids and chlorinated hydrocarbons.

2. The process of claim 1 wherein said dialkylarylketone is 3,4,3',4'-tetramethylbenzophenone.

3. The process of claim 1 wherein said dialkylarylketone is 4,4'-dimethylbenzophenone.

4. The process of claim 1 wherein said heating is effected at a temperature of about 140° to about 300° C.

5. The process of claim 1 wherein said heating is effected at a temperature of about 160° to about 225° C.

6. The process of claim 1 wherein the product obtained upon said heating involves dissolving in said solvent, in which said 1,1-diaryl-2-nitroethylene is soluble, at a temperature of about 26° to about 200° C., cooling to a temperature of about 0° to about 100° C. until solid dialkylarylketone precipitates out of solution and then recovering said dialkylarylketone from said solution.

7. The process of claim 1 wherein the product obtained upon said heating involves dissolving in said solvent, in which said 1,1-diaryl-2-nitroethylene is soluble, at a temperature of about 26° to about 100° C., cooling to a temperature of about 25° to about 45° C. until solid dialkylarylketone precipitates out of solution and then recovering said dialkylarylketone from said solution.

8. The process of claim 6 wherein said solvent is acetone.

9. The process of claim 6 wherein said solvent is acetic acid.

10. The process of claim 6 wherein said solvent is chlorobenzene.

11. The process of claim 1 wherein said heating is carried out in the presence of a solvent, in which said 1,1-diaryl-2-nitroethylene is soluble, the heated mixture is cooled to a temperature of about 0° to about 100° C. until solid dialkylarylketone precipitates out of solution and then recovering dialkylarylketone from said solution.

12. The process of claim 1 wherein said heating is carried out in the presence of a solvent, in which said 1,1-diaryl-2-nitroethylene is soluble, the heated mixture is cooled to a temperature of about 25° to about 45° C. until solid dialkylarylketone precipitates out of solution and then recovering dialkylarylketone from said solution.

13. The process of claim 11 wherein said solvent is acetone.

14. The process of claim 11 wherein said solvent is acetic acid.

15. The process of claim 11 wherein said solvent is ethyl chlorobenzene.

16. The process of claim 6 wherein the weight ratio of the heated product to the solvent is in the range of about 1:100 to about 1:1.

17. The process of claim 6 wherein the weight ratio of the heated product to the solvent is in the range of about 5:100 to about 1:4.

18. The process of claim 11 wherein the weight ratio of the heated product to the solvent is in the range of about 1:100 to about 1:1.

19. The process of claim 11 wherein the weight ratio of the heated product to the solvent is in the range of about 5:100 to about 1:4.

20. The process of claim 1 wherein said oily mixture is obtained as a result of the nitric acid oxidation of 1,1-bis(3,4-dimethylphenyl)ethane.

21. The process of claim 1 wherein said oily mixture is obtained as a result of the nitric acid oxidation of 1,1-bis(p-tolyl)ethane.

22. The process of claim 6 wherein said recovery is effected by filtration.

23. The process of claim 11 wherein said recovery is effected by filtration.

* * * * *